United States Patent [19]

Nishi et al.

[11] Patent Number: 5,006,353

[45] Date of Patent: Apr. 9, 1991

[54] PROCESS FOR THE PRODUCTION OF SURIMI

[75] Inventors: Norihisa Nishi; Makoto Nakamura; Satoshi Noguchi, all of Tokyo, Japan

[73] Assignee: Taiyo Fishery Co., Ltd., Tokyo, Japan

[21] Appl. No.: 426,969

[22] Filed: Oct. 25, 1989

[30] Foreign Application Priority Data

Jan. 12, 1989 [JP] Japan .................................. 64-5264

[51] Int. Cl.$^5$ ............................................. G01N 33/00
[52] U.S. Cl. ..................................... 426/231; 426/643
[58] Field of Search ....................... 426/231, 643, 657

[56] References Cited

U.S. PATENT DOCUMENTS 4,806,378 2/1989 Ueno et al. ........................... 426/643

Primary Examiner—George Yeung
Attorney, Agent, or Firm—Frishauf, Holtz, Goodman & Woodward

[57] ABSTRACT

A process for the production of a surimi which comprises distinguishing fish highly contaminated with sporozoans from less contaminated ones on the basis of the presence of cysts in fish meat; removing said highly contaminated fish; collecting fish meat from the residual fish; and leaching and dehydrating said fish meat. Thus a surimi of a high commercial value can be obtained by using fish which might be contaminated with sporozoans and thus frequently suffer from excessive softening as the starting material.

6 Claims, No Drawings

PROCESS FOR THE PRODUCTION OF SURIMI

BACKGROUND OF THE INVENTION

1. Field of the Invention

This invention relates to a process for the production of a surimi. More particularly, it relates to a process for the production of a surimi whereby a fish meat which frequently suffers from excessive softening caused by sporozoans can be effectively utilized.

2. Description of the Prior Art

Today, it is an important task to effectively utilize various shorefishes and demersal fishes which have been never utilized hitherto, because of various factors including the restriction of Japanese fishing areas. It has been known that fish contaminated with sporozoans would frequently suffer from excessive softening. These fish are lowly evaluated as a starting material in the production of processed marine products, since they show extremely poor elasticity and water retention, which are essential in the production of processed marine products, when formulated into a surimi. Under these circumstances, the present inventors have already provided some techniques which enable the production of a surimi of excellent qualities, for example, a process for improving fish meat qualities (cf. Japanese Patent Laid-Open No. 56269/1988).

Although the process cited above is an excellent one, the fish meat having qualities thus improved does not always have sufficient properties, including elasticity and water retention, for giving processed fish meat products of excellent qualities. Thus it has been demanded to develop a process for further improving fish meat qualities.

SUMMARY OF THE INVENTION

It is an object of the present invention to provide a process for the production of a surimi of such a high commercial value as comparable to that of Alaska pollack surimi which is widely marketed today by using a fish meat, which is contaminated with sporozoans and might suffer from excessive softening, as the starting material.

As a result of extensive studies, the present inventors have found that the presence of cysts formed by sporozoans in fish meat closely relates to the excessive softening of said fish meat caused by contamination with the sporozoans.

The object of the present invention, which has been completed based on the above finding, can be achieved by providing a process for the production of a surimi which comprises distinguishing fish highly contaminated with sporozoans from less contaminated ones depending on the presence of cysts; removing the highly contaminated fish; collecting fish meat from the less contamianted fish thus selected; leaching the fish meat with water and then dehydrating the same.

The present invention makes it possible to produce a surimi of a high commercial value which can impart a high elasticity and a high water retention to a processed product, even from fish meat which is contaminated with sporozoans and thus might frequently suffer from excessive softening. Therefore the present invention enables the effective utilization of Pacific hakes, Silver hakes, Offshore hakes, Panamanian hakes, Chilean hakes, Argentine hakes and so on, caught in North America or South America, which have been lowly evaluated as a starting material in the production of processed marine products. Thus the present invention is highly valuable from the viewpoint of economics as well as that of the effective utilization of resources.

DETAILED DESCRIPTION OF THE INVENTION

First, sporozoans will be briefly illustrated. Sporozoans are protozoans of several $\mu$m in size which cannot be observed with naked eyes. They are parasitic on various fishes including hake, flatfish, tuna and yellowtail and cause excessive softening of fish meat. Therefore a fish contaminated with sporozoans cannot be distinguished from uncontaminated ones in appearance. Thus there is no appreciable difference between fish liable to suffer from excessive softening and others.

Furthermore it is known that sporozoans would form cysts. Some cysts have a dark brown color, though it has not been obvious wheather a protease inducing the softening of fish meat is present in these dark brown sporangia or not. Thus the present inventors have examined the relationship between the activity of an enzyme inducing the softening of fish meat and these dark brown cysts. As a result, they have found that scarcely any cysts are observed in less contaminated fish while they become noticeable as the contamination proceeds.

They have further found that the activity of the softening enzyme of fish where the dark brown cysts are highly noticeable is several tens of times as high as that of commonly contaminated ones.

Based on these findings, the present inventors have established a process involving a distinguishing step where fish highly contaminated with sporozoans are removed on the basis of the presence of cysts. This process makes it possible to produce a fish meat or minced meat whose meat softening enzyme activity is 1/5 to 1/10 of that obtained by a conventional method.

Now the process for the production of a surimi according to the present invention will be described in detail. The presence of the dark brown cysts described above may be observed by some optical methods, for example, observing fish under natural or UV light. In a practical production system, various methods ranging from a manual one, wherein opened fillets are observed with naked eyes and those showing dark brown sporangia are removed with hands, to a fully automated one, wherein the occurrence of dark brown sporangia is confirmed by image analysis by scanning and highly contaminated ones are automatically removed from the production line, may be employed.

In addition to these optical methods, cysts can be detected by an ultrasonic imaging method. In this method, sporangia are observed as dark particles in somewhat light background, i.e., muscles. According to this method, not only the abovementioned dark brown cysts but also white ones, which can be hardly distinguished with naked eyes, can be detected.

A preferable example of the application of this ultrasonic imaging method to a practical production system may be conducted as follows. Namely, ultrasonic pulse is applied onto fillets on a conveyor and an ultrasonic signal reflected on the interface between a sporangium and a muscle, which are different in sonic impedance from each other, is received. Then the image is analyzed and any fillets having a large number of cysts are removed from the production line.

After removing highly contaminated fish by the abovementioned method, fish meat or minced meat collected from the residual starting fish is leached with water.

In the leaching step, it is preferable to use as much cold water as possible. However the leaching may be conducted by using the same amount of or twice as much water based on the fish meat.

The leaching water is not particularly restricted. It is preferable to use a calcium salt solution, since the removal ratio of the softening enzyme, the leaching efficiency, the dehydrating efficiency and an increase in elasticity are considerably improved thereby as compared with the case where water is used for leaching. These effects are found by the present inventors for the first time. When a calcium salt solution is to be employed, the concentration of the calcium salt should be appropriately adjusted in order to give a surimi of excellent qualities. It preferably ranges from 0.01 mM to 100 mM. Examples of the available calcium salt include calcium chloride, calcium chloride dihydrate, calcium citrate, calcium glycerophosphate, calcium gluconate, calcium hydroxide, calcium lactate, calcium dihydrogenpyrophosphate, calcium monohydrogenphosphate and calcium dihydrogenphosphate.

In the leaching step, the leaching solution to be mixed with the fish meat or minced meat should have a pH value of 6.0 to 8.0. When the pH value of the leaching soltuion does not fall within this range, it is impossible to produce a surimi of excellent qualities. This pH value range also applies to a case where a calcium salt solution is employed in the leaching step.

The temperature of the leaching solution is preferably 15° C. or below, though it is not restricted thereby. When the temperature of the leaching solution exceeds 15° C., the softening of the fish meat supposedly caused by sporozoans would become conspicuous, which might make the subsequent dehydration difficult. In the present invention, it is preferable that not only the leaching step but also the whole process involving the storage of the starting fish and the packing of the obtained surimi is carried out at a temperature of 0° to 15° C., still preferably 0° to 10° C.

After the completion of the leaching, the fish meat (minced meat) is then dehydrated. The dehydration may be conducted by any method without restriction. However it is preferable to dehydrate the fish meat in such a manner as to adjust the moisture content of the fish meat to 68 to 92%.

In the present invention, the dehydrated meat may be blended with sugars, which are commonly used as additives, as well as 0.12 to 10% by weight, on a dry basis, of bovine, swine, sheep, chicken or fish serum protein or plasma protein optionally together with 0.4% or below, on a dry basis, of albumen to thereby further improve the elasticity and water retention of the surimi. Thus the commercial value of the surimi product can be preferably enhanced. These additives are preferably added immediately after the completion of the dehydration, though it is not restricted thereby. When the amount of the above additive(s) is less than 0.1% on a dry basis, the effect cannot be fully achieved. When it exceeds 10%, on the other hand, the odor and texture of the resulting product might become undesirable.

To further illustrate the effect of the process of the present invention, the following Examples will be given.

In these Examples, each physical property was determined with a rheometer (mfd. by Fudo Kogyo K.K.) with a plunger of 5 mm in diameter.

Example 1

100 pacific hakes caught in North America were processed into fillets. The presence of dark brown sporangia in each fillet was observed with naked eyes to reveal that 16 fish carried dark brown cysts while 84 carried none. After removing those carrying the dark brown cysts, minced meat was collected from the residual fish. Separately, another minced meat was collected without removing the cyst-carrying fish, for comparison. Each minced meat was stirred together with twice as much water for five minutes and then dehydrated. Thus two minced meats, each having a moisture content of 82%, were obtained. The temperature in the system was controlled in such a manner that every step until the dehydration was conducted at 15° C. or below. Further care was taken in order to prevent any unusual rise of the temperature of the meat.

To 100 parts by weight of each dehydrated meat were added four parts by weight of sorbitol and four parts by weight of sucrose. Thus two surimi products, namely, one obtained from the starting material free from any cyst-carrying fish and another obtained from starting material including the cyst-carrying fish were obtained. Some portion of each surimi was frozen at $-30°$ C. and stored to thereby given a frozen surimi product.

Thus four products, namely, unfrozen and frozen surimis obtained from dark brown cyst-free fish and those obtained from dark brown cyst-carrying fish were prepared. To 100 parts by weight of each product was added three parts of common salt (NaCl). The obtained mixture was filled in a casing (folding diameter: 47 mm), allowed to stand at 5° C. overnight and heated to 90° C. for 40 minutes to thereby give a processed fish meat product. Then the physical properties including break strength and depression of each product were determined. Furthermore the elasticity of the same was organoleptically evaluated. Table 1 summarizes the results. The organoleptical evaluation was conducted by six skilled panelists of Taiyo Fishery Co., Ltd. on the basis of ten points. The evaluation is expressed in the mean, the same will apply hereinafter.

TABLE 1

| Surimi | Break strength (g) | | Depression (mm) | | Organoleptic evaluation | |
|---|---|---|---|---|---|---|
| | unfrozen | frozen | unfrozen | frozen | unfrozen | frozen |
| Cyst-carrying | 165 | 60 | 5 | 5 | 0 | 0 |
| Cyst-free | 650 | 620 | 13 | 12.5 | 6 | 6 |

Thus it was found that the elasticity of the surimi of the invention obtained from the starting material from which the dark brown cyst-carrying fish had been removed was much higher than that of the one obtained from the starting material including the dark brown cyst-carrying fish.

Example 2

100 pacific hakes caught in North America were employed. The presence of cysts in these fish was examined by an ultrasonic imaging method with the use of a sector electronic scanning device EUB-150 (mfd. by Hitachi Medico Co.) to reveal that 25 fish carried cysts while 84 carried none. After removing those carrying the cysts, minced meat was collected from the residual fish. Separately, minced meat was collected without removing the cyst-carrying fish, for comparison. Each minced meat was stirred together with twice as much water for five minutes and then dehydrated. Thus two minced meats, each having a moisture content of 82%, were obtained. The temperature in the system was controlled in such a manner that every step until the dehydration was conducted at 15° C. or below. Further care was taken in order to prevent any rise of the temperature of the meat.

To 100 parts by weight of each dehydrated meat were added four parts by weight of sorbitol and four parts by weight of sucrose. Thus two surimi products, namely, one obtained from the starting material free from any cyst-carrying fish and another obtained from starting material including the cyst-carrying fish were obtained. Some portion of each surimi was frozen at −30° C. and stored to thereby give a frozen surimi product.

Thus four products, namely, unfrozen and frozen surimis obtained from dark brown cyst-free fish and those obtained from dark brown cyst-carrying fish were prepared. To 100 parts by weight of each product was added three parts of common salt (NaCl). The obtained mixture was filled in a casing (folding diameter: 47 mm), allowed to stand at 5° C. overnight and heated to 90° C. for 40 minutes to thereby give a processed fish meat product. Then the physical properties including break strength and depression of each product were determined. Furthermore the elasticity of the same was organoleptically evaluated. Table 2 summarizes the results.

TABLE 2

| Surimi | Break strength (g) | | Depression (mm) | | Organoleptic evaluation | |
|---|---|---|---|---|---|---|
| | un-frozen | frozen | un-frozen | frozen | un-frozen | frozen |
| Cyst-carrying | 165 | 60 | 5 | 5 | 0 | 0 |
| Cyst-free | 850 | 820 | 14 | 14.5 | 7 | 7 |

Thus it was found that the elasticity of the surimi of the invention obtained from the starting material from which the cyst-carrying fish had been removed was much higher than that of the one obtained from the starting material including the dark brown cyst-carrying fish.

Example 3

Pacific hakes caught in North America were employed. Those carrying dark brown cysts were removed in the same manner as the one described in Example 1. Fish meat collected from the residual fish was homogeneously mixed and divided into two portions. One of these portions was mixed with twice as much water while the other was mixed with a twice as much 1 mM solution of CaCl$_2$.2H$_2$O. Each mixture thus obtained was stirred for five minutes and then dehydrated. Thus dehydrated meats having a moisture content of 82% and 81% were obtained. Similar to Example 1, the total process was conducted at a temperature of 15° C. or below and care was taken in order to inhibit an unusual rise of the meat temperature.

To 100 parts by weight of each dehydrated meat were added four parts by weight of sorbitol and four parts by weight of sucrose to thereby give a surimi product. These products will be referred to as the water-leached surimi and the Ca-treated surimi hereinafter. To 100 parts by weight of each surimi was added three parts by weight of common salt (NaCl). The obtained processed fish meat products were tested in the same manner as the one described in Example 1. Table 3 summarizes the results.

To 100 parts by weight of each surimi was added two parts by weight of a spray-dried bovine plasma protein powder. Subsequently three parts by weight of common salt (NaCl) was further added thereto. These products were subjected to the same test as the one described above. Table 3 also shows the results.

TABLE 3

| Surimi | Break strength (g) | | Depression (mm) | | Organoleptic evaluation | |
|---|---|---|---|---|---|---|
| | not added | added | not added | added | not added | added |
| Water-leached | 630 | 850 | 12.5 | 13.0 | 6.0 | 8.0 |
| Ca-treated | 700 | 1100 | 13.5 | 14.5 | 8.0 | 9.0 |

Table 3 obviously indicates that the elasticity of the Ca-treated surimi was much higher than that of the water-leached one; and that the addition of the bovine plasma protein further elevated the elasticity. The elasticity of the latter case was nearly comparable to that of an Alaska pollack surimi.

The pacific hakes subjected to the selection by the ultrasonic imaging were also tested in the same manner, though the obtained data are not shown in the above Table. As a result, the break strength, depression and organoleptic evaluation increased by 200 g, approximately 1 mm and approximately one point, respectively, compared with the above data. These facts also provied the effectiveness of the Ca treatment and the addition of the bovine plasma protein.

Example 4

Pacific hakes caught in North America were employed and those carrying dark brown cysts were removed in the same manner as the one described in Example 1. Fish meat collected from the residual fish was homogeneously mixed and divided into two portions. One of these portions was mixed with twice as much water, stirred for five minutes and then dehydrated, while maintaining the temperature below 10° C. The other portion was treated in the same manner as the one described above, except that the temperature was 25° C. (room temperature). Thus dehydrated meats, each having a moisture content of 82%, were obtained.

To 100 parts by weight of each dehydrated meat were added four parts by weight of sorbitol and four parts by weight of sucrose to thereby give a surimi product.

To 100 parts by weight of each surimi was added three parts by weight of common salt (NaCl). The obtained mixture was filled in a casing (folding diameter: 47 mm) to thereby give a processed fish meat product in the same manner as the one described in Example 1. These products were subjected to the same test as the one described above. Table 4 summarizes the results.

TABLE 4

| Processed at | Break strength (g) | Depression (mm) | Organoleptic evaluation |
|---|---|---|---|
| 10° C. or below | 650 | 12.5 | 6 |
| 25° C. | 500 | 11.0 | 5 |

The 10° C. process could be normally operated. On the other hand, the surimi became a muddy mass in the 25° C. process, which made the dehydration highly difficult. As shown in Table 4, the elasticity of the surimi obtained by the 25° C. process was obviously lower than that of the one obtained by the 10° C. process.

Pacific hakes, from which cyst-carrying ones had been removed by the ultrasonic imaging, were subjected to the same test as the one described above. As a result, a similar tendency to the abovementioned one was observed.

What is claimed is:

1. In a process for the production of a surimi, which comprises distinguishing fish highly contaminated with sporozoans from less contaminated ones; removing said highly contaminated fish; collecting fish meat from the residual fish; and processing the residual fish into surimi, the improvement comprising
   determining the presence of cysts in the fish meat as a basis for identifying highly contaminated fish for removal before collecting the fish meat from the residual fish, and thereafter leaching and dehydrating said fish meat.

2. A process for the production of a surimi as set forth in claim 1, wherein the presence of said cysts is determined by an ultrasonic imaging method.

3. A process for the production of a surimi as set forth in claim 1, wherein the presence of said cysts, which are dark brown ones, is determined by observing with naked eyes or by an optical method.

4. A process for the production of a surimi as set forth in claim 1, wherein the collected fish meat or minced meat is leached with water and dehydrated in such a manner as to give a moisture content of 68 to 92% by weight and then 0.1 to 10% by weight, on a dry basis, of serum protein or plasma protein is added thereto.

5. A process for the production of a surimi as set forth in claim 1, wherein said leaching is carried out by using a calcium salt solution of a pH value of 6.0 to 8.0 and a concentration of 0.01 mM to 100 mM and the leached fish meat or minced meat is dehydrated in such a manner as to give a moisture content of 68 to 92% by weight, followed by addition of 0.1 to 10% by weight, on a dry basis, of serum protein or plasma protein thereto.

6. A process for the production of a surimi as set forth in claim 1, wherein the whole process is carried out at a temperature of 0° to 15° C.

* * * * *